United States Patent [19]

Abou-Gharbia et al.

[11] Patent Number: 4,777,254
[45] Date of Patent: Oct. 11, 1988

[54] CYCLIC IMIDES AS H1-ANTAGONISTS
[75] Inventors: Magid A. Abou-Gharbia; Susan T. Nielsen, both of Wilmington, Del.
[73] Assignee: American Home Products Corp., New York, N.Y.
[21] Appl. No.: 937,167
[22] Filed: Dec. 2, 1986
[51] Int. Cl.$^4$ .......................................... C07D 403/06
[52] U.S. Cl. .................... 544/230; 544/361; 544/362; 544/372; 544/373; 544/403; 546/15; 546/16; 546/76; 546/79; 546/97; 546/183; 546/200; 546/272; 546/273; 548/424
[58] Field of Search ............... 544/230, 361, 362, 372, 544/373

[56] References Cited
U.S. PATENT DOCUMENTS

| | | | |
|---|---|---|---|
| 3,398,051 | 8/1968 | Wu | 544/230 |
| 4,006,233 | 2/1977 | Shepard et al. | 514/272 |
| 4,261,990 | 4/1981 | Bowman | 514/183 |
| 4,423,049 | 12/1983 | Temple | 544/230 |
| 4,435,419 | 3/1984 | Epstein et al. | 514/412 |
| 4,507,303 | 3/1985 | Ishizumi et al. | 544/230 |
| 4,524,206 | 6/1985 | New et al. | |
| 4,562,255 | 12/1985 | Freed et al. | 544/373 |
| 4,598,078 | 7/1986 | Ishizumi et al. | 544/373 |

FOREIGN PATENT DOCUMENTS
113226A1 12/1983 European Pat. Off. .

OTHER PUBLICATIONS
Wu et al., J. Med. Chem. p. 876 (1969).

Primary Examiner—Donald G. Daus
Assistant Examiner—E. Bernhardt
Attorney, Agent, or Firm—Richard K. Jackson

[57] ABSTRACT

Polycyclic 1,3-dione imides N-alkylated with variously N-substituted alkyl- or cycloalkyl amines afford histamine H1-receptor antagonists of the formula

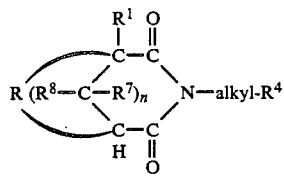

wherein
R is polycyclic alkyl moiety;
$R^1$ is hydrogen or alkyl;
$R^4$ is an aromatic amine or a cycloalkyl amine containing N-substitution;
$R^7$ and $R^8$ are hydrogen, alkyl or form a spiro cycloalkyl group.

5 Claims, No Drawings

CYCLIC IMIDES AS H₁-ANTAGONISTS

BRIEF DESCRIPTION OF THE INVENTION

Polycyclic 1,3-dione imides N-alkylated with variously N-substituted alkyl- or cycloalkyl amines afford histamine H₁ receptor antagonists of the formula

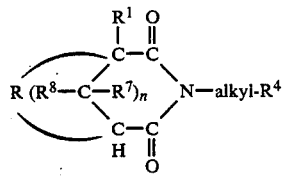

where
R is a polycyclic alkyl moiety;
$R^1$ is hydrogen or alkyl;
$R^4$ is an aromatic amine or a cycloalkyl amine containing N-substituent;
$R^7$ and $R^8$ are hydrogen, alkyl or form a spiro cycloalkyl group.

DETAILED DESCRIPTION OF THE INVENTION

In accordance with this invention, there is provided histamine H₁-receptor antagonists of the formula:

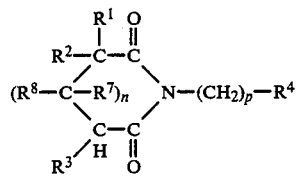

in which
(a) n is 0, $R^1$ is hydrogen, and $R^2$ and $R^3$, taken together, are

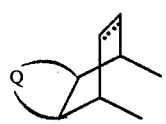

where Q is alkylene of 0 to 4 carbon atoms or alkenylene of 2 to 4 carbon atoms and the dotted line represents optional unsaturation; or
(b) n is 1, $R^1$, $R^7$ and $R^8$ are alkyl of 1 to 3 carbon atoms and $R^2$ and $R^3$, taken together, are alkylene of 2 to 4 carbon atoms; or
(c) n is 1, $R^1$, $R^2$ and $R^3$ are hydrogen and $R^7$ and $R^8$, taken together, are cycloalkyl of 2 to 5 carbon atoms;
(d) n is 1, $R^7$ and $R^8$ are hydrogen or alkyl of 1 to 3 carbon atoms, $R^1$ is hydrogen, $R^2$ and $R^3$, taken together, are cycloalkylene of 5 to 7 carbon atoms;
$R^4$ is

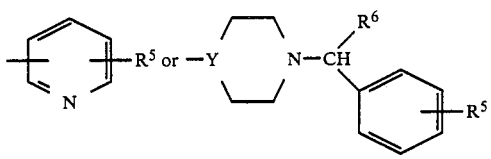

where
Y is carbon or nitrogen,
$R^5$ is hydrogen, alkyl of 1 to 6 carbon atoms, halo, cyano, nitro or trifluoromethyl,
$R^6$ is hydrogen or

and p is one of the integers 2, 3, 4 or 5 when Y is nitrogen, or p is one of the integers 0, 1, 2, 3, 4, or 5 when Y is carbon;
or a pharmaceutically acceptable salt thereof.

The compounds of this invention are prepared by conventional methods. For example, either the imidic nitrogen of the 1,3-dione imide or the amine present in $R^4$ is alkylated with a difunctional alkylating agent such as X—(CH₂)p—X where X is a halogen, and subsequently the other nitrogen atom is alkylated, thusly:

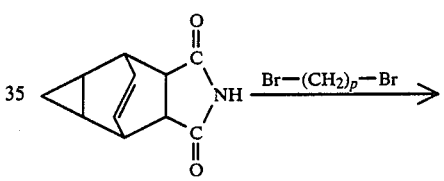

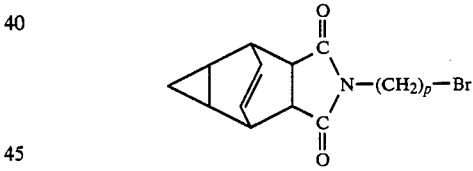

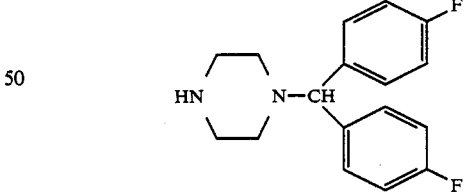

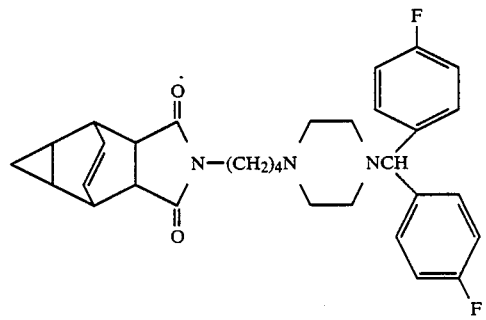

Alternatively, a suitable dicarboxylic acid anhydride, such as camphoric anhydride, is reacted with the desired amine $H_2N-(CH_2)_p-R^4$ to produce the N-substituted 1,3-dione imide.

The starting materials employed to produce the compounds are either known compounds or may be produced by conventional methods. For example, the initial reactant employed in Example 1, infra, is the Diehls-Alder adduct of 1,3,5-cycloheptatriene and maleic acid imide.

The pharmaceutically acceptable salt of the anti-histaminic agents of this invention are prepared by conventional means with inorganic or organic acids such as hydrochloric, hydrobromic, sulfuric, phosphoric, nitric, acetic, fumaric, citric, tartaric, maleic, lactic, 2-hydroxyethanesulfonic, methanesulfonic, toluene-4-sulfonic, ethanesulfonic acid, and the like.

The compounds of this invention were established to be histamine $H_1$-receptor antagonists by subjecting them to the following standard test procedure for $H_1$-blocking activity:

Fresh segments of terminal ileum immediately proximal to Peyer's patch, obtained from male Buckshire guinea pigs, were suspended in 37° C. Tyrode's solution in a tissue bath and aerated. The tissue segments were placed under one gram tension and allowed to equilibrate for one hour. Histamine was added to each tissue bath to a final concentration of $1 \times 10^{-7}M$. The response was noted as grams tension. Test drug was added, in the presence of histamine, to each bath to a final concentration of $1 \times 10^{-6}M$ with the compounds of Examples 1 and 2 and $1 \times 10^{-7}M$ for the other exemplified compounds. The change in grams tension was noted and the percent reduction in grams tension calculated. The percent reduction in tension for each compouond exemplified herein is given at the end of each preparative example. The results obtained in accordance with this procedure establishd that the compounds exhibit a potent antagonist action against the histamine-induced contractile response in the isolated guinea pig ileum.

The pharmacological results obtained characterize the compounds of this invention as $H_1$-receptor antagonists useful in the treatment of conditions such as asthma, conjunctivitis, pruritis, hay fever, allergic rhinitis, atopic dermatitis and eczema. As such, they may be administered topically or systemically. Topical administration is advantageously achieved to the skin via creams, ointments or lotions, or via aerosol introduction into the respiratory tract. Systemic administration may be orally, parenterally or rectally. In each instance, conventional formulations amenable to use in the desired administration route is appropriate. Hence, tablets and capsules may be prepared for oral administration, suppositories for rectal administration and isotonic aqueous solutions for intravenous, subcutaneous or intramuscular injection.

As is conventional in the use of antihistaminic agents, the appropriate dosage is determined on a subjective basis by initial administration of small amounts, ca. 1–15 mg. followed by increasing quantities up to about 400 mg. by topical, oral or rectal routes and about 200 mg. intravenous, until the desired symptomatic relief is obtained. The dosage is personalized in this manner for each patient, based upon size, age, type of discomfort, degree of disability etc. by the physician.

The following examples are presented to illustrate the preparation of representative compounds of this invention.

EXAMPLE 1

2-[4-[4-[bis(4-fluorophenyl)methyl]-1-piperazinyl]-butyl]-4,4a,5,5a,6,6a-hexahydro-4,6-ethenocycloprop[f]isoindole-1,3-(2H,3aH)-dione To a stirred solution of 3.4 g (0.017 mol) of 1,3-dioxo-2H-4,6-etheno-1,3,3a,6a-tetrahydrocycloprop[f]isoindole in 50 ml of dimethylformamide is added 0.9 g of sodium hydride. The suspension is stirred at 60° C. for 3 hours and is poured into a stirred solution of 1,4-dibromobutane (4 g, 0.02 mol) in 25 ml of dimethylformamide.

The reaction mixture is stirred at room temperature for 24 hours, dimethylformamide is evaporated under reduced pressure and the residue is extracted with methylene chloride ($3 \times 200$ ml). The methylene chloride extracts are collected, washed with water, dried over anhydrous $Na_2SO_4$ and evaporated under reduced pressure. The residue is solidified to a waxy material affording 3.6 g (67% yield) of the corresponding 2-(4-bromobutyl)hexahydro-4,6-ethenocycloprop[f]isoindole-1,3(2H,3H)-dione.

The title compound is prepared by dissolving 2.5 g (0.007 mol) of 2-(4-bromobutyl)hexahydro-4,6-ethenocycloprop[f]isoindole-1,3(2H,3H)-dione in 50 ml of dimethylformamide, and to this solution is added 6 ml of triethylamine and 2 g (0.007 mol) of 1-bis(4-fluorophenyl)methylpiperazine. The reaction mixture is stirred at room temperature for 48 hours. The dimethylformamide is removed under reduced pressure and the remaining solid is extracted with $2 \times 100$ ml of methylene chloride.

The methylene chloride extracts are collected, dried over anhydrous $Na_2SO_4$ and evaporated in vacuo. The remaining oil was triturated with ethyl acetate: diethyl ether (1:1 mixture) and the title compound was separated by filtration and converted to the dihydrochloride salt by dissolving in ethanol and adding to that solution 2 ml of ethanol saturated with hydrogen chloride, mp 218°–220° C.

Analysis for: $C_{32}H_{35}N_3F_2O_2 \cdot 2HCl \cdot \frac{1}{2}H_2O$: Calculated: C, 62.59; H, 6.19; N, 6.84; Cl, 11.57; Found: C, 62.99; H, 6.30; N, 6.32; Cl, 11.29

Reduction of guinea pig ileum tension=98%.

EXAMPLE 2

2-[4-[4-bis(4-fluorophenyl)methyl]-1-piperazinyl]-propyl]-4,4a,5,5a,6,6a-hexahydro-4,6-ethenocycloprop[f]isoindole-1,3-(2H,3aH)-dione The title compound was prepared following procedure of Example 1 using 1,3-dibromopropane instead of 1,4-dibromobutane and was converted to the dihydrochloride salt; mp 239°–240° C.

Analysis for: $C_{31}H_{33}N_3F_2O_2 \cdot 2HCl \cdot \frac{1}{2}H_2O$: Calculated: C, 62.10; H, 6.10; N, 7.01; Found: C, 62.22; H, 61.5; N, 7.03

Reduction in guinea pig ileum tension=25%

EXAMPLE 3

8-[4-[4-[bis(4-fluorophenyl)methyl]-1-piperazinyl]-butyl]-8-azaspiro[4.5]decane-7,9-dione The title compound was prepared following procedure of Example 1 using 3,3-tetramethyleneglutarimide instead of 1,3-dioxo-2H-4,6-etheno-1,3,3a,6a-tetrahydrocycloprop[f]isonidole and was converted to the hydrochloride salt; mp 165°-169° C.

Analysis for: $C_{30}H_{37}F_2N_3O_2 \cdot 2HCl \cdot 2H_2O$: Calculated: C, 59.11; H, 6.88; N, 6.89; Cl, 11.65; Found: C, 58.75; H, 6.34; N, 6.80; Cl, 11.68

Reduction in guinea pig ileum tension=77%

EXAMPLE 4

1,8,8-Trimethyl-3-[2-(2-pyridinyl)ethyl]-3-azabicyclo[3.2.1]octane-2,4-dione

A mixture of (−) camphoric anhydride 5 g (0.029 mol), 2-(2-aminoethyl)pyridine 3.6 (0.03 mol) and 50 ml of pyridine was refluxed overnight. The solvent is removed under reduced pressure and the remaining oil boiled in 20 ml of ethanol and allowed to cool.

The separated solid was filtered and dried; mp 80°-81° C.

Analysis for: $C_{17}H_{22}N_2O_2$: Calculated: C, 71.08; H, 8.01; N, 9.75; Found: C, 71.11; H, 7.74; N, 9.65

Reduction in guinea pig ileum tension=38%

EXAMPLE 5

4,4a,5,5a,6,6a-Hexahydro-2-[2-(2-pyridinyl)ethyl]-4,6-ethenocycloprop[f]isoindole-1,3(2H,3H)dione The title compound was prepared following procedure of Example 4 using tricyclo[4.2.1.0]non-3-en-8,9-dicarboxylic anhydride instead of (−) camphoric anhydride and was converted to the hydrochloride salt; mp 215°-217° C.

Analysis for: $C_{18}H_{18}N_2O_2 \cdot HCl$; Calculated: C, 65.35; H, 5.79; N, 8.47; Found: C, 65.50; H, 5.76, N, 8.45

Reduction in guinea pig ileum tension=36%

EXAMPLE 6

2-[3-[4-[(4-chlorophenyl)phenylmethyl]-1-piperazinyl]-propyl]-4,4a,5,5a,6,6a-hexahydro-4,6-ethenocycloprop[f]isoindole-1,3(2H,3aH)-dione The title compound was prepared following proceodure of Example 1, using 1-[(4-chlorophenyl)phenyl]methyl piperazine instead of 1-bis(4-fluorophenyl)methylpiperazine and was converted to the dihydrochloride salt; mp 150°-157° C.

Analysis for: $C_{31}H_{34}ClN_3O_2 \cdot 2HCl \cdot 2H_2O$: Calculated: C, 59.54; H, 6.45; N, 6.72; Found: C, 60.56; H, 6.36; N, 7.94

Reduction in guinea pig ileum tension=29%

EXAMPLE 7

3-[1-[(4-fluorophenyl)methyl]-4-piperidinyl]-1,8,8-trimethyl-3-azabicyclo[3.2.1]octane-2,-dione The title compound was prepared by refluxing a mixture of (−) camphoric anhydride 5 g (90.029 ml), 4-aminopyridine 2.8 g (0.03 ml) and 50 ml of pyridine overnight. The solvent was removed under reduced pressure and the remaining oil was dissolved in 20 ml of ethanol-hydrogenchloride solution and was hydrogenated using 0.8 g of $RhlAl_2O_3$ overnight. The solvent was removed under reduced pressure to afford 3-(4-piperidinyl)-1,8,8-trimethyl-3-azabicyclo[3.2.1]octane-2,4-dione-hydrochloride.

The title compound was prepared by stirring 2 g (0.005 ml) of the above intermediate and 0.99 g (0.005 ml) of 4-fluorobenzylbromide in 50 ml of dimethylformamide at 60° C. overnight in the presence of 6 ml. of triethylamine. The product was worked up following the procedure of Example 1 to afford 1 g of the title compound which was converted to the hydrochloride salt; mp 288°-290° C.

Anlaysis for: $C_{22}H_{29}FN_2O_2 \cdot HCl$: Calculated: C, 64.77; H, 7.41; N, 6.87; Found: C, 64.36; H, 7.28, N. 6.79

Reduction in guinea pig ileum tension=24%

What is claimed is:

1. A compound of the formula:

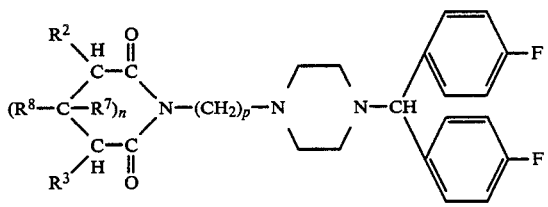

in which
(a) n is 0 and $R^2$ and $R_3$, taken together are

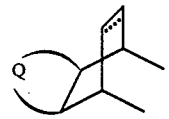

where Q is alkylene of 0 to 4 carbon atoms or alkenylene of 2 to 4 carbon atoms and the dotted line represents optional unsaturation;

or (b) n is 1, $R^2$ and $R^3$ are hydrogen and $R^7$ and $R^8$, taken together, are polymethylene of 2 to 5 carbon atoms;

and p is one of the integers 2, 3, 4 or 5;

or a pharmaceutically acceptable salt thereof.

2. A compound of the formula:

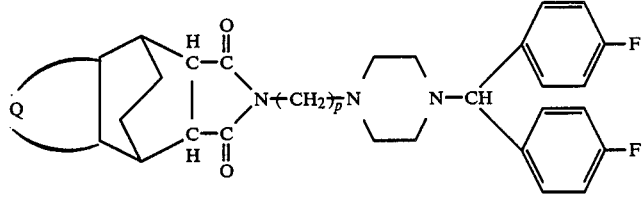

in which
the dotted line represents optional unsaturation;
Q is alkylene of 0 to 4 carbon atoms or alkenylene of 2 to 4 carbon atoms; and
p is one of the integers 2, 3, 4 or 5;
or a pharmaceutically acceptable salt thereof.

3. A compound of claim 1 which is 2-[4-[4-[bis(4-fluorophenyl)methyl]-1-piperazinyl]butyl]-4,4a,5,5a,6-

,6a-hexahydro-4,6-ethenocycloprop[f]isoindole-1,3-(2H,3aH)-dione, or a pharmaceutically acceptable salt thereof.

4. A compound of claim 1 which is 2-[4-[4-bis(4-fluorophenyl)methyl]-1-piperazinyl]propyl]-4,4a,5,5a,6,6a-hexahydro-4,6-ethenocycloprop[f]isoindole-1,3-(2H,3aH)-dione, or a pharamecutically acceptable salt thereof.

5. A compound of claim 1 which is 8-[4-[4-[bis(4-fluorophenyl)methyl]-1-piperazinyl]butyl]-8-azaspiro[4.5]decane-7.9-dione, or a pharamaceutically acceptable salt thereof.

* * * * *